(12) United States Patent
Aslanis-Aslanidis et al.

(10) Patent No.: US 9,757,030 B2
(45) Date of Patent: Sep. 12, 2017

(54) SYSTEM AND METHOD FOR THE DETERMINATION OF PARAMETERS OF EYE FIXATION

(71) Applicants: Ioannis Aslanis-Aslanidis, Heraklion (GR); Georgios Kaloutsakis, Heraklion (GR)

(72) Inventors: Ioannis Aslanis-Aslanidis, Heraklion (GR); Georgios Kaloutsakis, Heraklion (GR)

(73) Assignees: Ioannis Aslanis-Aslanidis, Heraklion (GR); Georgios Kaloutsakis, Heraklion (GR)

( * ) Notice: Subject to any disclaimer, the term of this patent is extended or adjusted under 35 U.S.C. 154(b) by 0 days.

(21) Appl. No.: 15/322,007

(22) PCT Filed: Jul. 2, 2015

(86) PCT No.: PCT/IB2015/055005
§ 371 (c)(1),
(2) Date: Dec. 23, 2016

(87) PCT Pub. No.: WO2016/001874
PCT Pub. Date: Jan. 7, 2016

(65) Prior Publication Data
US 2017/0135576 A1 May 18, 2017

(30) Foreign Application Priority Data

Jul. 3, 2014 (GR) .............................. 20140100362

(51) Int. Cl.
*A61B 3/14* (2006.01)
*A61B 3/113* (2006.01)
(Continued)

(52) U.S. Cl.
CPC ............ *A61B 3/113* (2013.01); *A61B 3/0025* (2013.01); *A61B 3/0091* (2013.01); *A61B 3/145* (2013.01);
(Continued)

(58) Field of Classification Search
CPC ... A61B 3/0025; A61B 3/0083; A61B 3/0091; A61B 3/113
(Continued)

(56) References Cited

U.S. PATENT DOCUMENTS

| 4,889,422 A | 12/1989 | Pavlidis | |
|---|---|---|---|
| 8,931,905 B2* | 1/2015 | Lewis | A61B 3/032 351/209 |
| 2013/0188834 A1* | 7/2013 | Ebisawa | A61B 3/113 382/103 |

FOREIGN PATENT DOCUMENTS

| EP | 1747750 A1 | 1/2007 |
|---|---|---|
| WO | 02/069788 A1 | 9/2002 |

(Continued)

OTHER PUBLICATIONS

Brown et. al. (1983) "Predictive eye-movements do not discriminate between dyslexic and control children," Neuropsychologia, vol. 21:2, 121-128.
(Continued)

*Primary Examiner* — Huy K Mai
(74) *Attorney, Agent, or Firm* — Brownstein Hyatt Farber Schreck LLP; Cara L. Crowley-Weber

(57) ABSTRACT

The invention refers to eye technology and in particular a system and method for the characterization of eye fixation. The invention further refers to a system and method for the determination of parameters of eye fixation and saccadic motions. The system and method may be used to diagnose and evaluate reading difficulties for ascertaining how much
(Continued)

benefit an individual would derive from an intervention with an expert, i.e. after treatment. A system for subject 10 eye tracking on a projection surface 6 includes: (i) infrared light source 3 to create reflections on the subject's eyes, (ii) two or more cameras 4 for subject's head position tracking, (iii) one or more cameras 4 to track movements of the subject's first eye on the projection surface, (iv) one or more cameras 4 to track movements of the subject's second eye on the projection surface 6, and (v) a processing unit 7 configured so that it tracks the subject's gazes on the projection surface, determines if the subject focuses on a predefined sub-region or sub-regions in the projection surface from the tracking of said gazes and computes the duration of said gazes.

16 Claims, 20 Drawing Sheets

(51) Int. Cl.
  *A61B 5/00* (2006.01)
  *A61B 5/11* (2006.01)
  *A61B 3/00* (2006.01)
(52) U.S. Cl.
  CPC .......... *A61B 5/0077* (2013.01); *A61B 5/1114* (2013.01); *A61B 5/1128* (2013.01); *A61B 2576/02* (2013.01)
(58) Field of Classification Search
  USPC .................................. 351/205, 209, 210, 211
  See application file for complete search history.

(56) References Cited

FOREIGN PATENT DOCUMENTS

| WO | 2004/093668 A1 | 11/2004 |
| WO | 2007/145566 A1 | 12/2007 |
| WO | 2008/091759 A1 | 7/2008 |
| WO | 2012/038676 A1 | 3/2012 |
| WO | 2014/041247 A1 | 3/2014 |

OTHER PUBLICATIONS

Handler, et al (2011) "Learning disabilities, dyslexia, and vision," Pediatrics 127, (3):E818-856.
Klassen (2002) "The Changing Landscape of Learning Disabilities in Canada: Definitions and Practice from 1989-2000," School Psychology International, 23:1-21.
Morris et al. (1993) "Eye movements in skilled reading: Implications for developmental dyslexia," Macmillan Press.
Rayner (1998) "Eye movements in reading and information processing: 20 years of research," Psycho Bull, 124 (3):372-422.
Stanley et. al. (1993) "Eye-movements and sequential tracking in dyslexic and control children," British Journal of Psychology 74:181-187.
Starr et al., (2001) "Eye movements during reading: some current controversies," Trends Cogn. Sci. Apr 1;5 (4):156-163.
Stein (1990) J.F. (Ed) "Vision and visual dyslexia," London: Macmillan Press.
International Search Report and Written Opinion for PCT/IB2015/055005, dated Oct. 10, 2015.

\* cited by examiner

SYSTEM AND METHOD FOR THE DETERMINATION OF PARAMETERS OF EYE FIXATION

This application is a National Stage Application of PCT/IB2015/055005 filed Jul. 2, 2015, which claims benefit of GR 20140100362, filed Jul. 3, 2014, both of which are incorporated herein by reference. To the extent appropriate, a claim of priority is made to each of the above disclosed applications.

The invention refers to eye technology and in particular a system and method for the characterization of eye fixation. The invention further refers to a system and method for the determination of parameters of eye fixation and saccadic motions. The system and method may be used to diagnose and evaluate reading difficulties for ascertaining how much benefit an individual would derive from an intervention with an expert, i.e. after treatment.

Standardized printed tests are being used for the evaluation and diagnosis of reading difficulties, such as dyslexia. During these tests the subject is evaluated by a specialist, usually a speech pathologist or a psychologist. Both the experience and the objectivity of the user/examiner/specialist play a very important role at the diagnosis result.

When a person reads a line of text, his/her eyes make a sequence of fixations. Fast movements between fixations are called saccades that accurately "guide" the eyes to an information-wise optimal landing point, literally the central part of our retina: the fovea. Foveal vision is a prerequisite for visual detail.

In terms of speed and accuracy, eye movement efficiency in reading develops almost in parallel with reading ability, as the child develops from a beginner to a skilled adult reader. Less skilled readers, for example young children, typically make more fixations of longer duration and shorter saccades than skilled readers [see Starr et al., *Eye movements during reading: some current controversies. Trends Cogn Sci.* April 1; 5(4):156-163 (2001)]. Although it has been suggested that "faulty" eye movements may cause reading problems, it is more likely that eye movements are a reflection of reading problems and not the cause of them [see Morris el al., *Eye movements in skilled reading: Implications for developmental dyslexia*. In Stein, J. F. (Ed.), *Vision and visual dyslexia*. London: Macmillan Press (1990)].

Given an individual's chronological age, measured intelligence, and age-appropriate education developmental dyslexia is characterized by reading achievement that falls substantially below than expected. This disturbance in reading significantly interferes with academic achievement or with activities of daily life that require reading skills [see ICD-10: F81.0]. Although there have been no studies to indicate an accurate percentage, dyslexia is the most common learning disability and the most recognized of reading disorders with an estimated prevalence of around 5-10% [see Handler. et al., *Learning disabilities, dyslexia, and vision. Pediatrics* 127 (3): e818-56) (2011)].

Various studies have highlighted the characteristics of dyslexic's eye movements that are specifically linked to reading. In general, children with developmental dyslexia, compared to their typically developing peers, have been reported to have more and longer fixations, shorter saccades and more regressions [see Rayner K. *Eye movements in reading and information processing:* 20 *years of research. Psychol Bull.* November; 124 (3):372-422 (1998)]. Most researchers agree that these differences in eye movement behavior are either correlated with the consequences of the reading difficulties experienced by children with dyslexia. In other words, eye movement behavior during reading could underline the characteristics of abnormal reading patterns in children with developmental dyslexia [see Morris el al., *Eye movements in skilled reading: Implications for developmental dyslexia*. In Stein, J. F. (Ed.), *Vision and visual dyslexia*. London: Macmillan Press (1990)].

Currently, methods for dyslexia diagnosis consist of a full psychological evaluation. In practice however, the lack of a common worldwide definition on the outcome and the causes of dyslexia results the lack of a definitive diagnostic approach. Thus, the specialist during the formal evaluation assesses a number of characteristics that may suggest if an individual is dyslexic.

Due to the lack of resources and experienced personnel a full psychological evaluation is available for a limited percentage of the population. Evaluation of dyslexia with objective measures, such as the eye movement pattern, will provide an efficient and fast method to discriminate children with or without reading difficulties.

Moreover, due to the fact that the definition of dyslexia among countries and languages differs, the diagnostic criteria differ as well. This situation undermines the credibility and integrity of any identification process, because it assumes a reading disability is therefore not permanent or intrinsic since it can be altered between different evaluations [see Klassen, R. M. *The Changing Landscape of Learning Disabilities in Canada: Definitions and Practice from* 1989-2000. *School Psychology International*, 23, 1-21 (2002)].

Commonly, a full psychological evaluation, the recommended method for diagnosing dyslexia, would be carried out by a trained administrator and would involve social and family history, cognitive testing, educational testing, school performance, educational performance evaluation and medical examinations. Due to time and cost limitations, such comprehensive testing is very rarely undertaken. Instead simpler and less time consuming screening tests are usually used to detect signs of dyslexia.

The main limitations of such screening tests are the following:

They Require Prior Knowledge or Expertise by Test Administrator:

Information generated by screening tests is valuable to teachers and trainers and can help them recognize signs or behavior linked with dyslexia or other reading difficulties. However, their interpretation requires expertise in education or psychology resulting in a high evaluation cost. Moreover, it is very difficult for non-experts to correctly identify potential signs of dyslexia or any of the other reading difficulties.

Lack of Adequate Objectiveness:

Most of these tests, especially those that are non-computer based, could be affected by external factors such as fatigue or mental state of the individual. Misinterpretation by the examiner is another limitation, which could lead to misdiagnosis. In addition, a re-evaluation of the individual could result in a different diagnosis since the aforementioned external factors may also vary.

Fail to Provide Specific Information for the Individual's Eye Movement Characteristics:

Most of the widely used screening tests can only provide general information and results by using a percentile ranking or a custom scale. Such classification cannot provide precise information about the individual's reading pattern in order for the therapist to create a custom made treatment plan.

Lengthy Tests can Cause Fatigue or Boredom to the Individual:

An evaluation for reading difficulties, for example dyslexia, is performed by using subtests that may be boring for the subject. This will lead to lack of attention which could afterwards result an inconclusive or false diagnosis by the examiner. In addition, the fact that in some cases the examiner is a doctor/therapist might cause stress to the subject.

Two devices/methods are currently associated with eye movements. The one is known as Visagraph and is based on data from 1985. The other is the Pavlidis' method. Both are based on recording eye movements that are not directly related to the vision projections over the reading surface.

Visagraph is a system that employs eye-tracking sensors for text reading and correlates the sensor readings with eye movements. Visagraph takes account only the subject's horizontal eye movements and therefore it does not record the full reading pattern of the individual. The method does not distinguish the difference between reading a text with five lines reading five times the same line.

Pavlidis' method uses a sequence of lights, which the subject is asked to follow with its eyes while the head remain steady. The method does not use text reading at all for the diagnosis, and for that reason it cannot incorporate the reading characteristics for evaluating reading difficulties in general. The method is discussed in Stanley et. al., *Eye-movements and sequential tracking in dyslexic and control children. British Journal of Psychology* 74, 181-187 (1993)& Brown et. al., *Predictive eye-movements do not discriminate between dyslexic and control children. Neuropsychologia*, vol 21, no. 2, 121-128 (1983).

It is worth mentioning that both methods require from the subject to wear a recording apparatus on his/hers head in order to record eye movements. These devices are uncomfortable for the subject, they can act as a distractive factor and may also narrow the visual field. These devices are different to the current invention, which does not require any kind of wearable equipment.

The object of the invention is a system and a method for the reliable and objective determination of parameters of eye fixation. A further object of the invention is a system and a method for the determination of parameters of eye fixation that does not require the subject to wear any special equipment. A further object of the invention is a system and a method for the determination of parameters of eye fixation, whereby the user/test-administrator/examiner does not require to be trained for long in order to use it.

A system for subject eye tracking on a projection surface according to the invention that includes: (i) infrared light source to create reflections on the subject's eyes, (ii) two or more cameras for subject's head position tracking, (iii) one or more cameras to track movements of the subject's first eye on the projection surface, (iv) one or more cameras to track movements of the subject's second eye on the projection surface, and (v) a processing unit configured so that it tracks the subject's gazes on the projection surface, determines if the subject focuses on a predefined sub-region or sub-regions in the projection surface from the tracking of said gazes and computes the duration of said gazes.

The projection surface may present a text including a plurality of words and the processing unit may be configured so that it determines from the gaze tracking, if the subject focuses on certain words in the projection surface, and it computes the duration of these gazes on said words. To determine if the subject focuses on certain words, the processing unit may use the data related the tracking of the gazes of one eye or of both eyes of the subject. Preferably, the processing unit may be configured to determine at least one of the following: the duration of all fixations in multiply fixated words at first pass, the number of fixations in multiply fixated words at first pass, the number of single fixated words at first pass, the number of multiple fixated words at first pass, the number of skipped words at first pass of said sub-region, the sum of all fixation times on a particular word, including regressive fixations. "First passage" designates the first time that a fixation is being detected on a word/sub-region or word, "single fixated words" designates words/sub-regions that have a single fixation on the first passage occurred and "multiple fixation words" designates words/sub-regions that have more than a single fixation on the first passage occurred. For example, if a word is being "read" twice by a subject with one fixation occurring on the first passage and two fixations occur the second time than the word is read, the word is being considered as a single fixated word.

Optionally, the cameras for tracking the subject's first and second eye's movements on the projection surface may be also used for the subject's head tracking and the processing unit is configured so that it determines motions of the subject's head. Further, the cameras for tracking the subject's first and second eye's movements on the projection surface may be movable, preferably on a movable arm with sensors to monitor the position of the cameras relative to the projection surface, so that they are always at a known position relative to the projection surface. Preferably the cameras may track said gazes with a sampling rate between 30 Hz and 1000 Hz, indicative sampling rates are 30 HZ, 60 Hz, 90 Hz and 120 Hz. In this case the processing may compute the duration of said gazes with a rate that equal or lower to the sampling rate and preferably about the same as the sampling rate. However, cameras with sampling rates outside the preferable range of 30 Hz to 1000 Hz may be used. It is noted that a sampling rate of 1000 Hz corresponds to one measurement per ms.

A method according to the invention, includes the following steps: (i) using of a projection surface that includes text with words and/or shapes and/or numbers and/or images and/or video with the projection surface being printed or electronically displayed, (ii) determining parameters of fixations on predefined sub-regions or sub-regions inside the projection surface, and (iii) determining parameters of gaze movements inside the projection surface from the fixations parameters. Preferably, the method according to the invention is performed using a system according to the invention. It is noted that the "gaze movement" refers to the movement of the gaze on the projection surface.

The method may include the determination of saccadic motion parameters, preferably the length of the saccadic motion, from the gaze tracking of at the least one eye. The parameters of the saccadic motion may be used for the computation of the number and duration of fixations. Other parameters that may be determined by a method according to the invention are: the number and/or duration of fixations on the projection surface or on the same sub-region of the projection surface, at least one of the number, duration, direction and the length of eye movements, mean values and/or standard deviation of the fixation parameters and/or gaze movements on the projection surface, parameters of Gaussian exponential distributions for the number of fixations and/or gaze movements inside the projection surface, average values and/or standard deviation and/or parameters of Gaussian exponential distributions for the saccadic motion parameters.

The system and the method according to the invention monitor and record the eye movements and all the characteristics while a subject reads or interacts with a stimulus, and based on these characteristics it can analyze, evaluate and help the diagnosis of the reading difficulties that the individual might have. The term "subject" describes the person, whose eye's or eyes' movements are monitored. The term "individual" is any person, who may be a user or a user as such.

The system and method according to the invention is fast, objective and has measurable results with high reproducibility. The method is applied in an entirely standardized manner to all individuals, enhancing the reliability measurement. Duration of fixations and saccadic motions of the stimuli can be determined precisely. In addition, the method for the determination of parameters of eye fixation is much faster than conventional printed tests, when used to diagnose and evaluate reading difficulties and for ascertaining how much benefit an individual would derive after treatment. The results can be compared with any pre- or post-assessment. Moreover, the diagnosis is objective because it is based on reading parameters, namely, fixation duration and saccadic length. The final outcome of the diagnosis cannot be affected by external factors, such as the subjective judgment of the test administrator. The system and method according to the invention may be also used for the evaluation and testing ergonomic parameters of text displaying, development of reading techniques and marketing.

In comparison with conventional printed tests using stop watches, the invention evaluates and analyzes only the real reading time due to the fact that the system can discard, with an accuracy of milliseconds, the time that the individual was not reading. By constantly recording the eye movements of the subject, all the data that are not related with the reading task and can lead to misdiagnosis are discarded.

Using the invention, reading data can be, for the first time, scrutinized by the administrator, as data can be analyzed even in milliseconds and evaluate reading abnormalities within words smaller than 10 letters. For the first time, the combination of several different reading parameters is transformed into a diagnostic tool.

The application of the system and the method does not require any particular expertise or prior knowledge and the only prerequisites for the user are basic computer and communication skills. The method is straightforward and is designed to be used by easily administrated by professionals coming from a variety of different backgrounds. Due to the examination method's simplicity and the automatically generated results report, there is no need for highly trained personnel. The subject's performance results and the graphical patterns will be generated automatically and no prior training would is required for the reading of the results. This fact reduces the cost of the evaluation.

The system and the method use video-based eye-tracking, a technology applied in computer science for research and marketing purposes. With a system and a method according to the invention the subject's reading characteristics can be thoroughly analyzed, with accuracy of millisecond. The information exported can be used for the diagnosis of reading abnormalities and difficulties both in children and adults. Fixation and saccade characteristics, such as means, standard deviations, fitting parameters, along with Ex-Gaussian distribution parameters are being measured. Contrary to the teaching or the prior art the invention considers both the horizontal and the vertical eye movements and records the full reading pattern of the individual.

The system and the method further provide specialized information for a customizable treatment by therapist. After thorough analysis of the results, the most common mistakes during test reading, as well as other problem to the reading process of the individual, may be identified by the method according to the invention. This knowledge is made available to the therapist who then can choose the appropriate personalized treatment. After a certain period, the individual can be re-evaluated using the initial or an updated reading test. The method is able to evaluate the progress of the individual's reading maturity over the years, using its standardized procedure.

The results obtained by the system and the method according to the invention are reproducible. The method had been tested on two consecutive evaluations of the same individual with 10-15 days intervals. This time period is short for any developmental changes on the individual. There was no significant difference between these two evaluations, indicating that the results are reproducible for the same subject.

The system and the method according to the invention may be applied to different languages. For each language a database needs to be developed and used for each language with the reading characteristics being calibrated for the given reading language. Each individual is evaluated based on the language database that he/she belongs to.

Optional features that are related with further advantages of the invention are defined in the dependent claims. The system and method for the characterization of eye fixation according to the invention may comprise one or more of the optional features in combination.

Embodiments of the invention are described below with reference to FIGS. 1 to 22, whereby:

Figure 5:
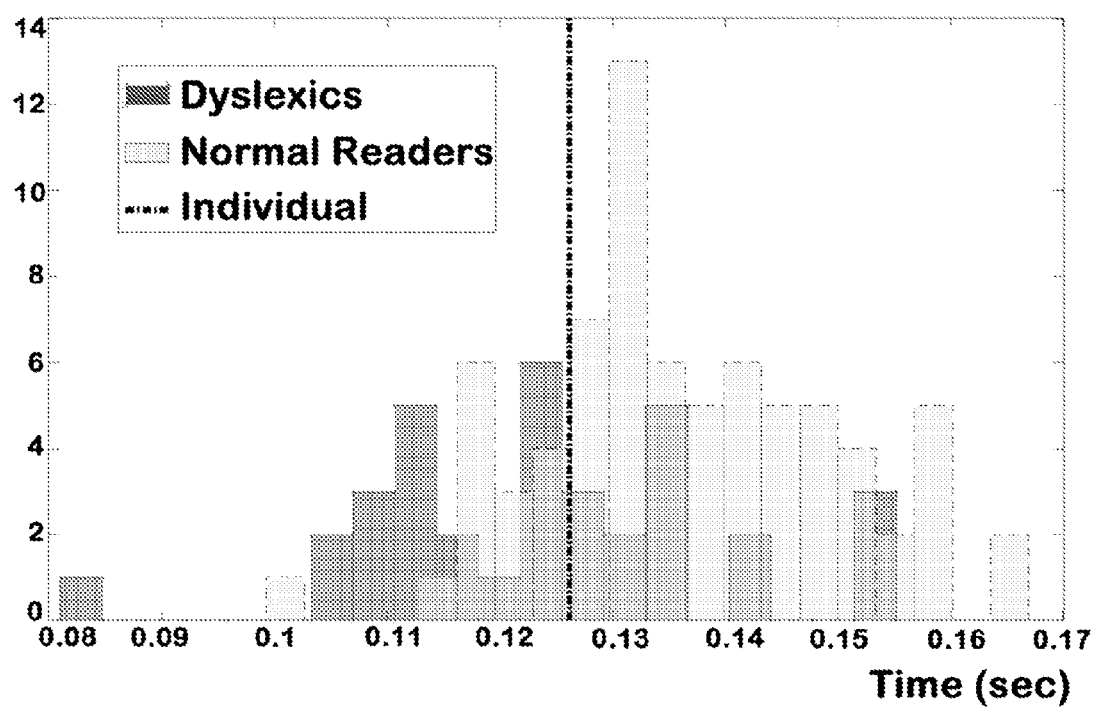
Figure 6:
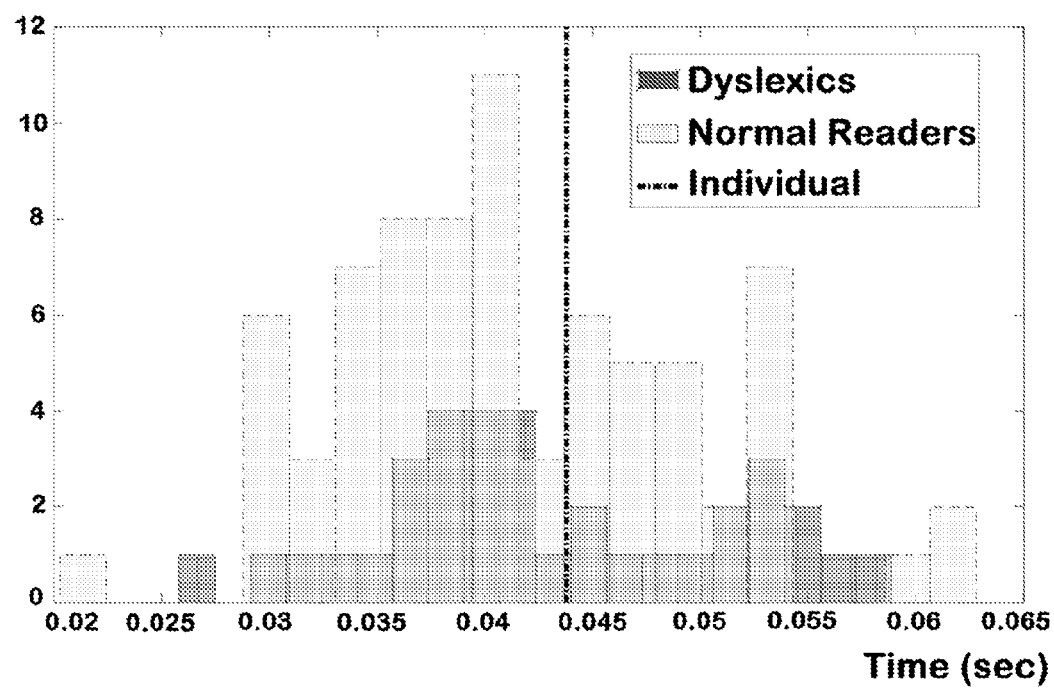

FIG. 5 is a graph showing the Ex-Gaussian parameter mu ($\mu$) of fixation durations, exhibited in the eye movements of people with reading difficulties and normal readers as obtained from the application of the method FIG. 6 is a graph showing the Ex-Gaussian parameter sigma ($\sigma$) of fixation durations, exhibited in the eye movements of people with reading difficulties and normal readers as obtained from the application of the method.

Figure 7:
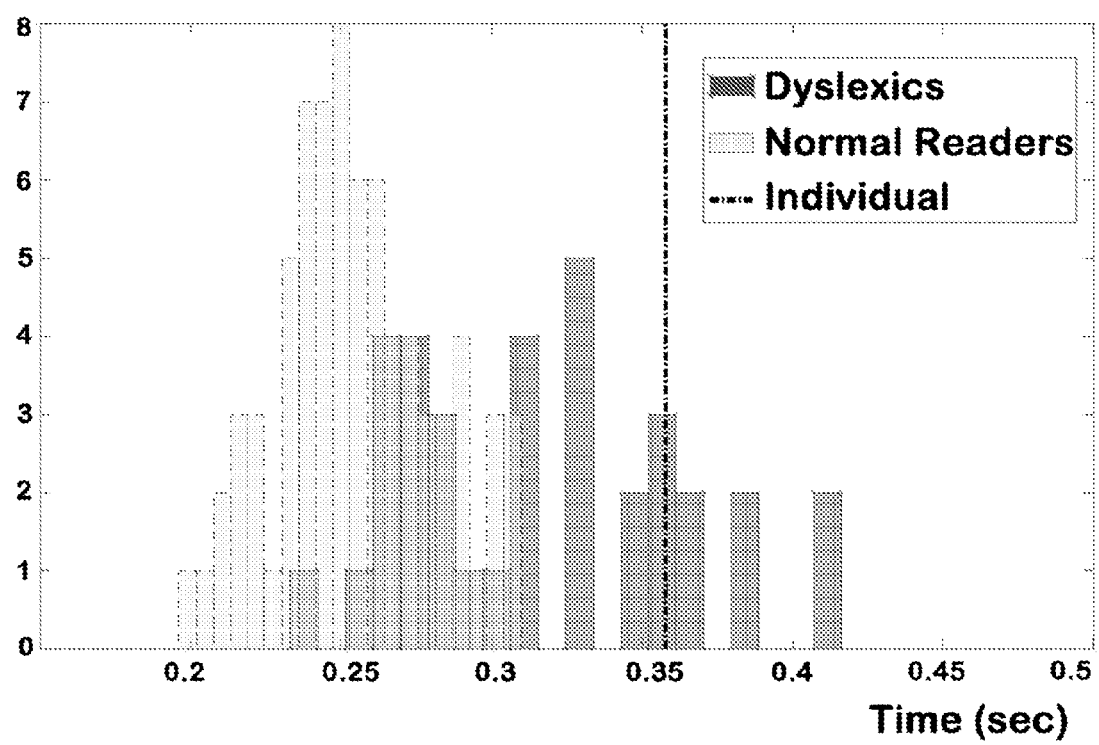
Figure 8:
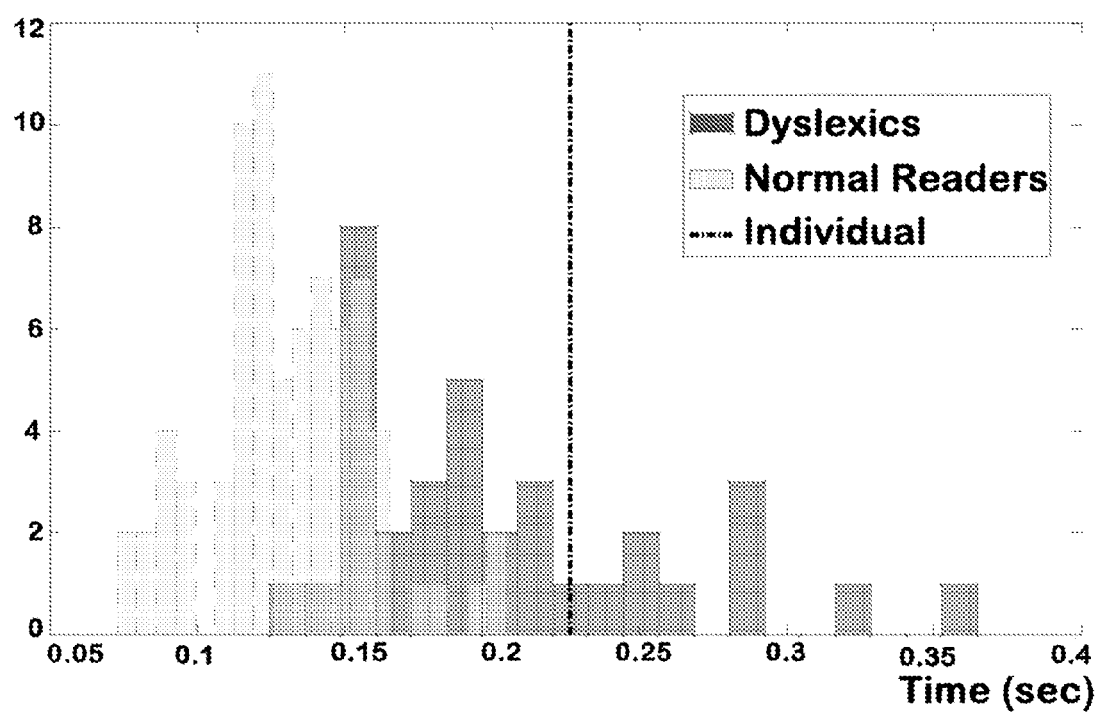

FIG. 7 is a graph showing the mean of fixation durations, exhibited in the eye movements of people with reading difficulties and normal readers as obtained from the application of the method FIG. 8 is a graph showing the standard deviation of fixation durations, exhibited in the eye movements of people with reading difficulties and normal readers as obtained from the application of the method.

Figure 9:
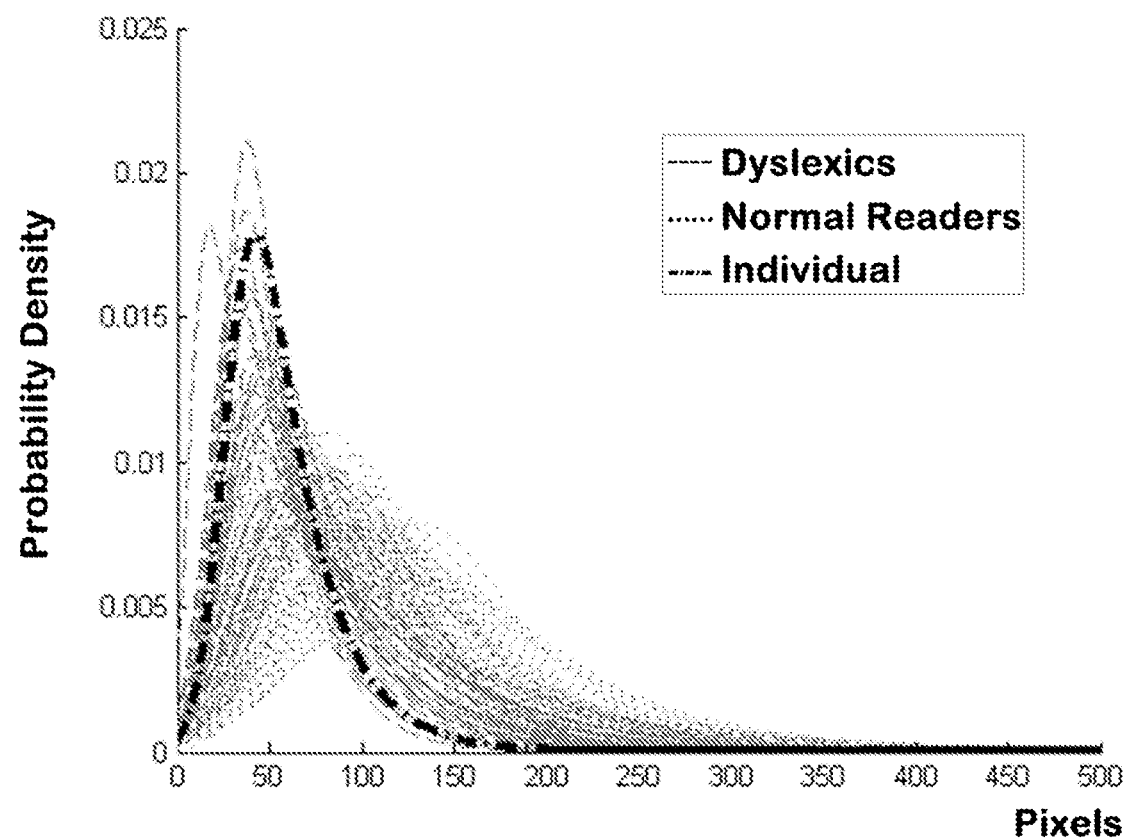

FIG. 9 is a graph showing the Ex-Gaussian curves of saccadic lengths, exhibited in the eye movements of people with reading difficulties and normal readers as obtained from the application of the method.

Figure 10:
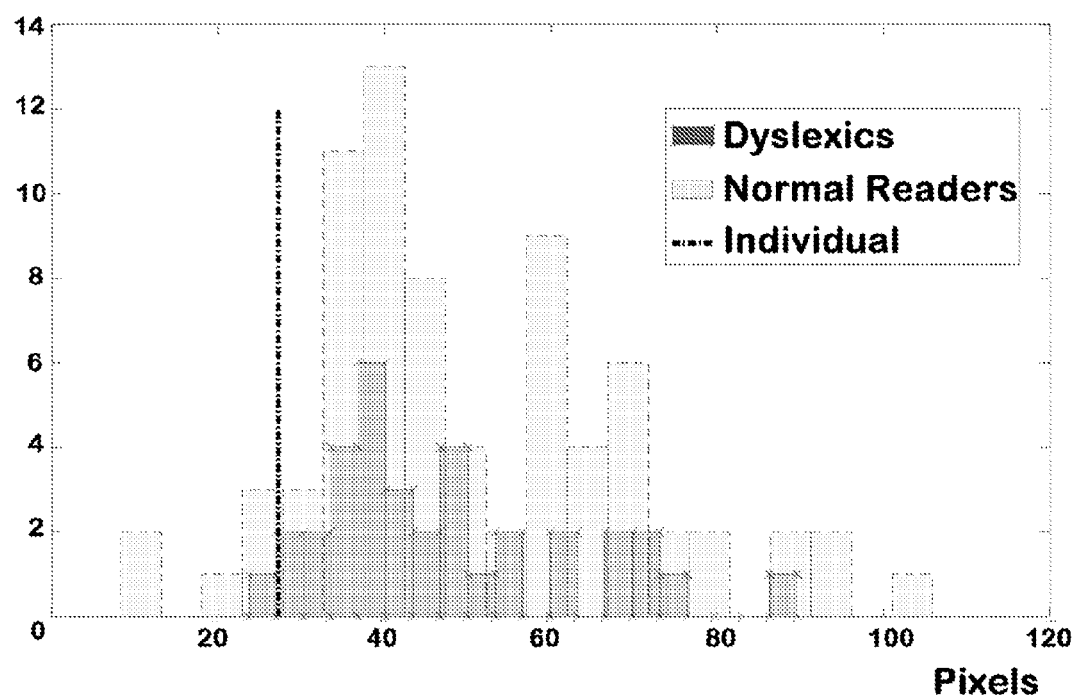

FIG. 10 is a graph showing the Ex-Gaussian parameter tau ($\tau$) of saccadic lengths, exhibited in the eye movements of people with reading difficulties and normal readers as obtained from the application of the method.

Figure 11:
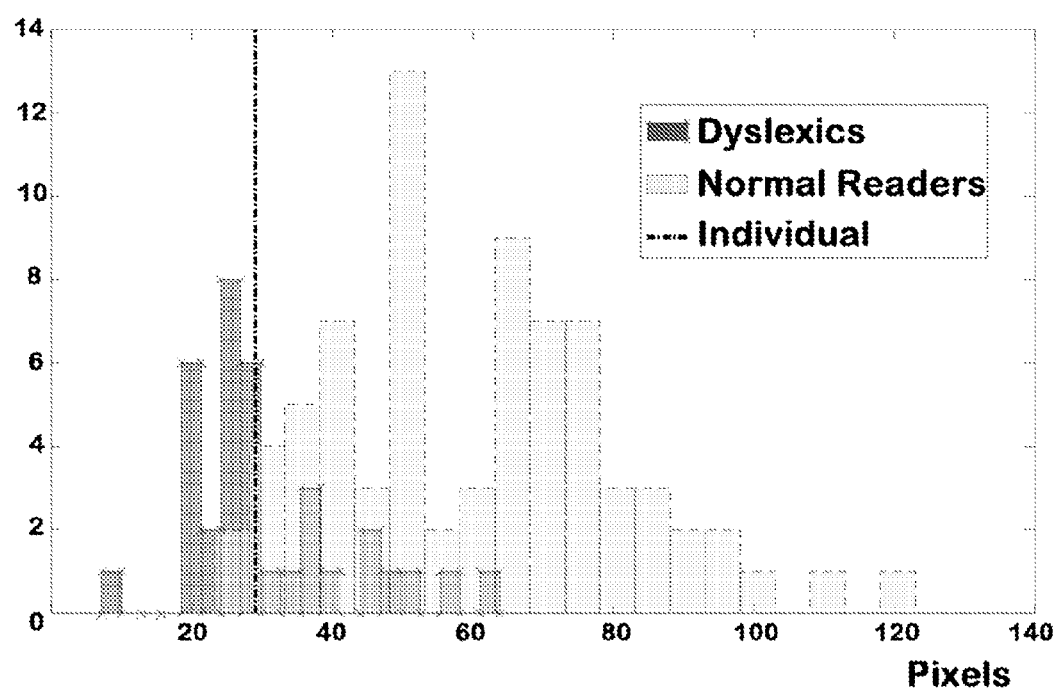

FIG. 11 is a graph showing the Ex-Gaussian parameter mu (μ) of saccadic lengths, exhibited in the eye movements of people with reading difficulties and normal readers as obtained from the application of the method.

Figure 12:
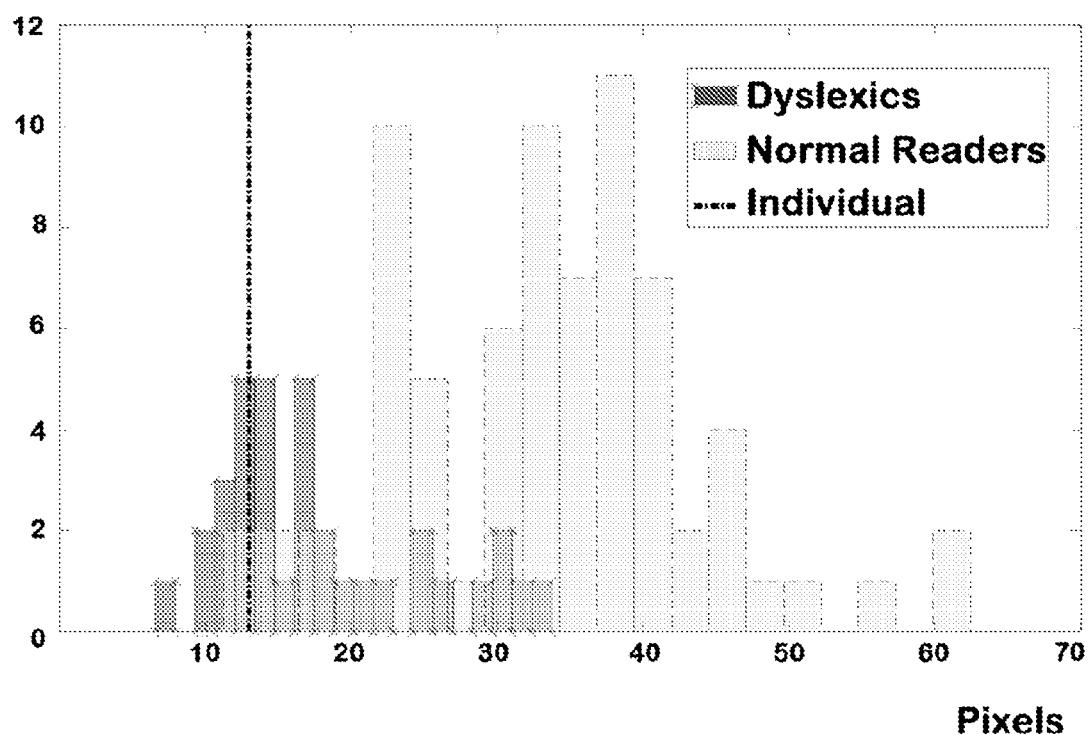

FIG. 12 is a graph showing the Ex-Gaussian parameter sigma (σ) of saccadic lengths exhibited in the eye movements of people with reading difficulties and normal readers as obtained from the application of the method.

Figure 13:
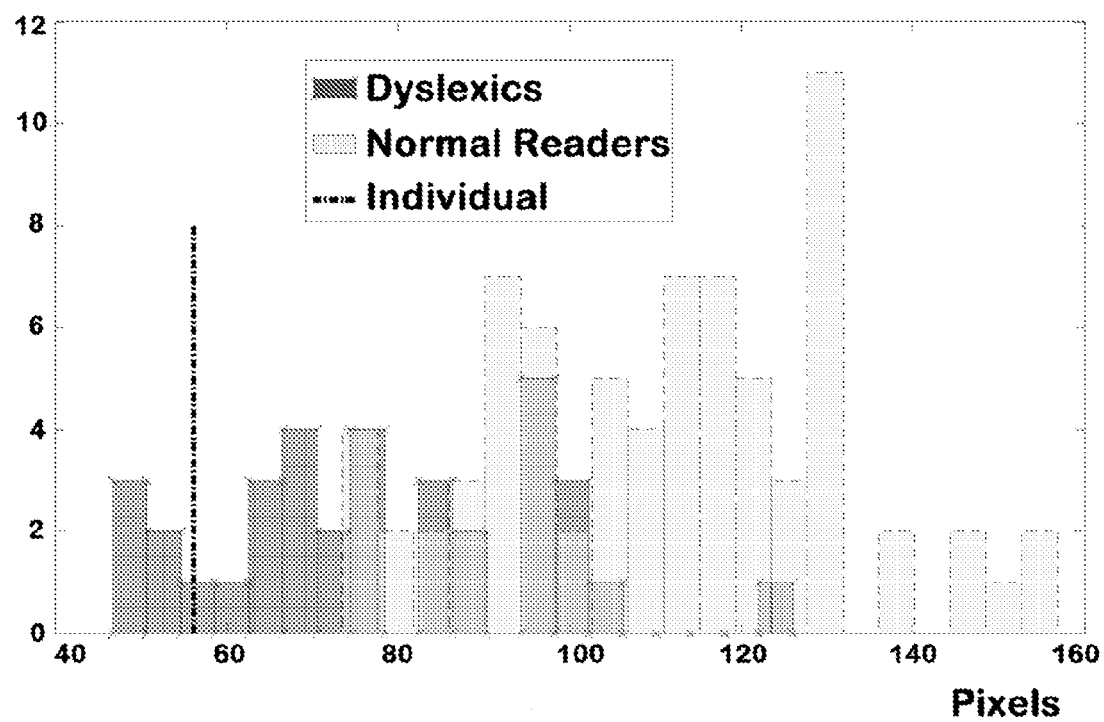

FIG. 13 is a graph showing the mean of saccadic lengths exhibited in the eye movements of people with reading difficulties and normal readers as obtained from the application of the method.

Figure 14:
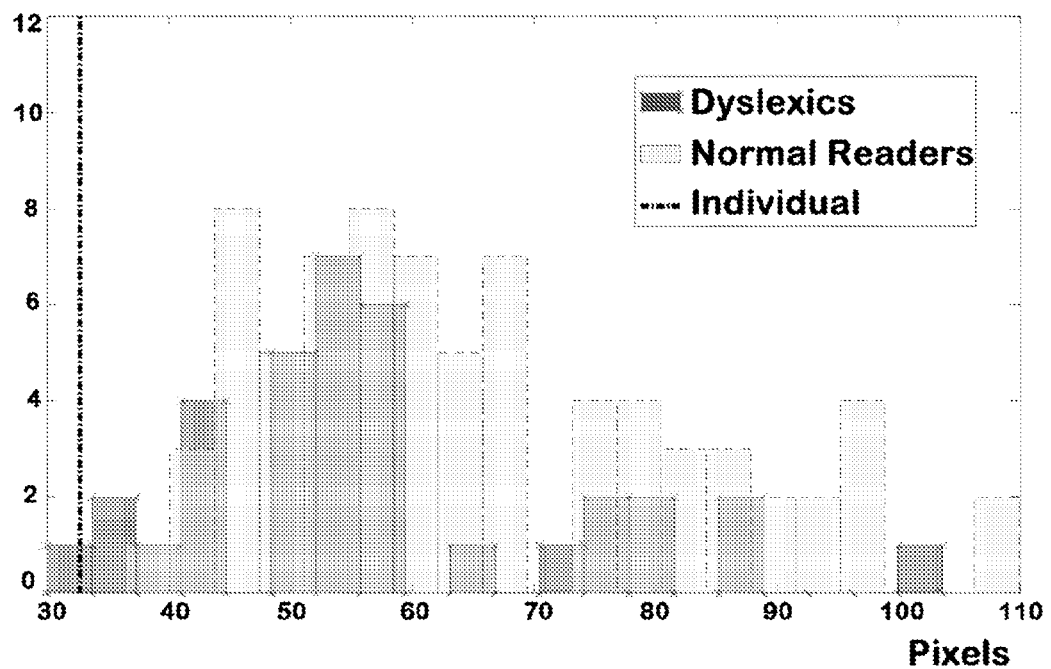
Figure 15:
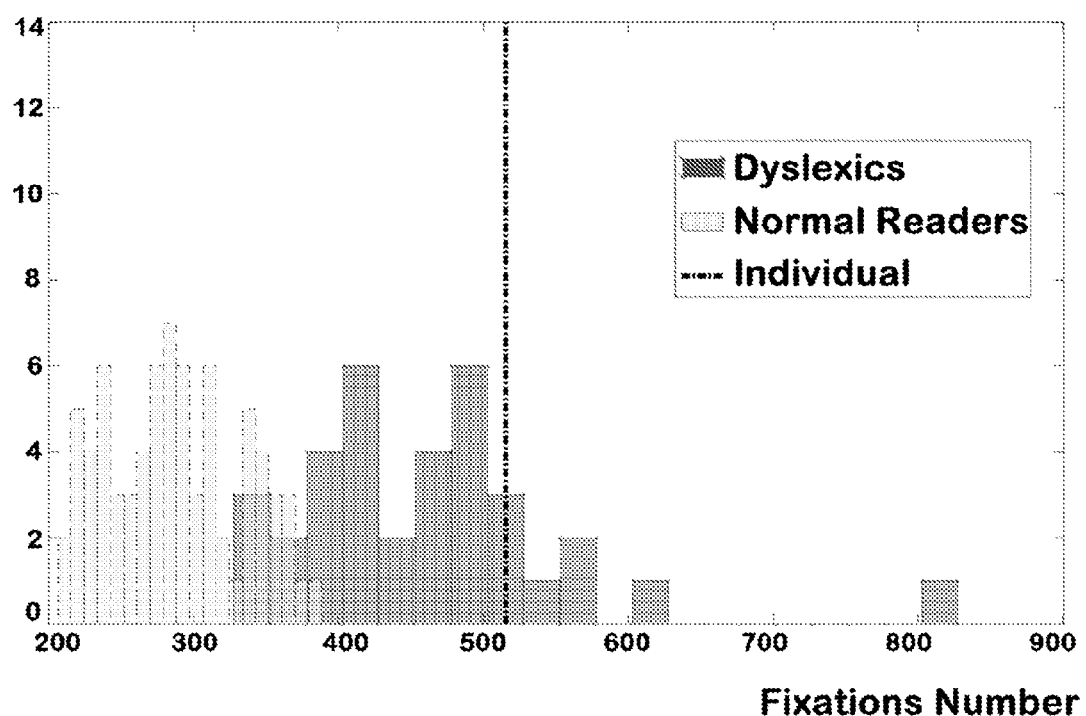

FIG. 14 is a graph showing the standard deviation of saccadic lengths, exhibited in the eye movements of people with reading difficulties and normal readers as obtained from the application of the method FIG. 15 is a graph showing the number of fixations, exhibited in the eye movements of people with reading difficulties and normal readers as obtained from the application of the method.

Figure 16:
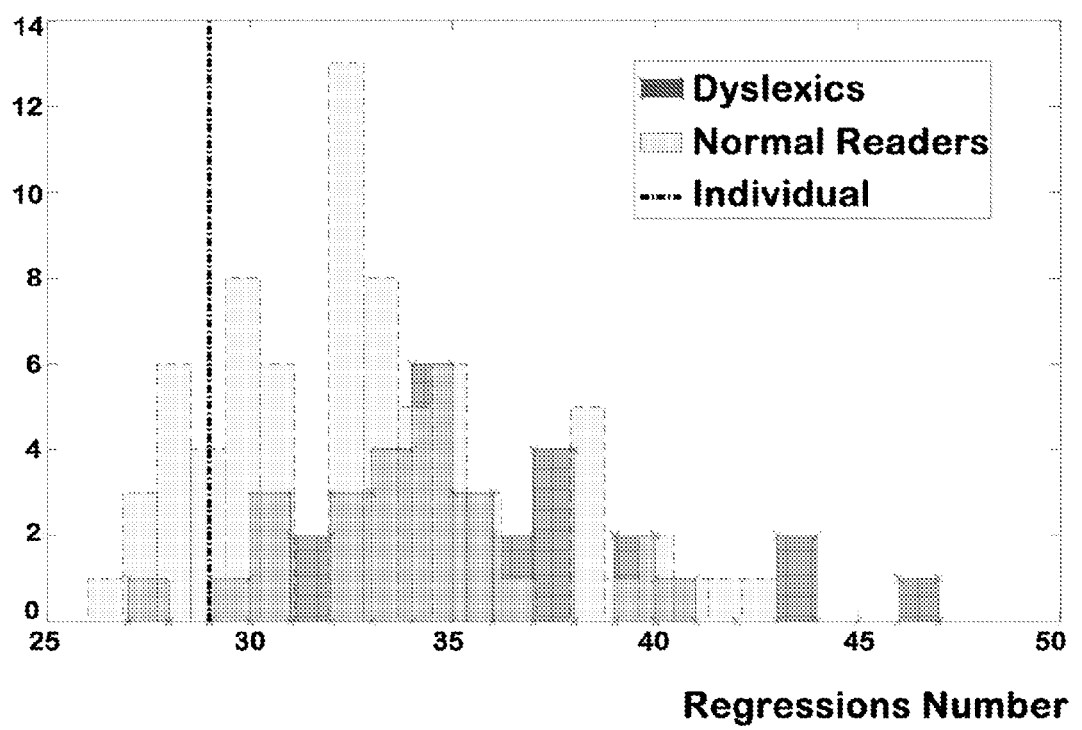

FIG. 16 is a graph showing the number of regressions, exhibited in the eye movements of people with reading difficulties and normal readers as obtained from the application of the method.

Figure 17:
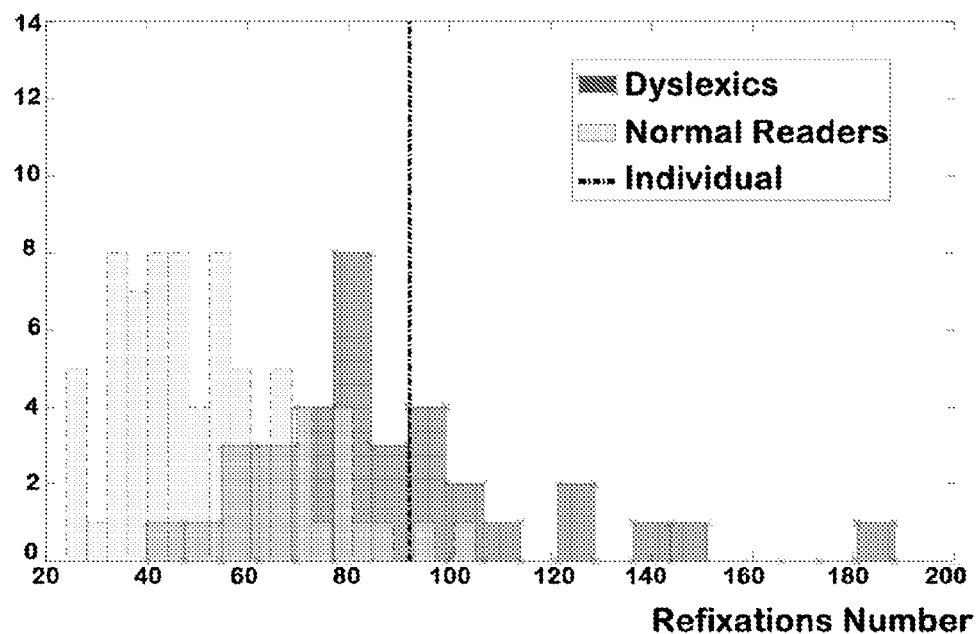

FIG. 17 is a graph showing the number of re-fixations, exhibited in the eye movements of people with reading difficulties and normal readers as obtained from the application of the method.

Figure 18:
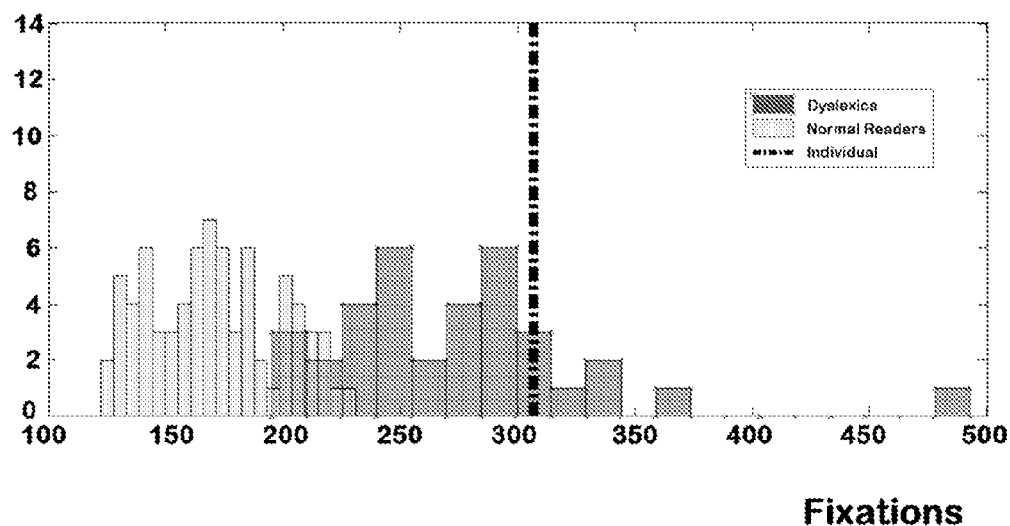

FIG. 18 is a graph showing the number of fixations per 100 words, exhibited in the eye movements of people with reading difficulties and normal readers as obtained from the application of the method.

Figure 19:
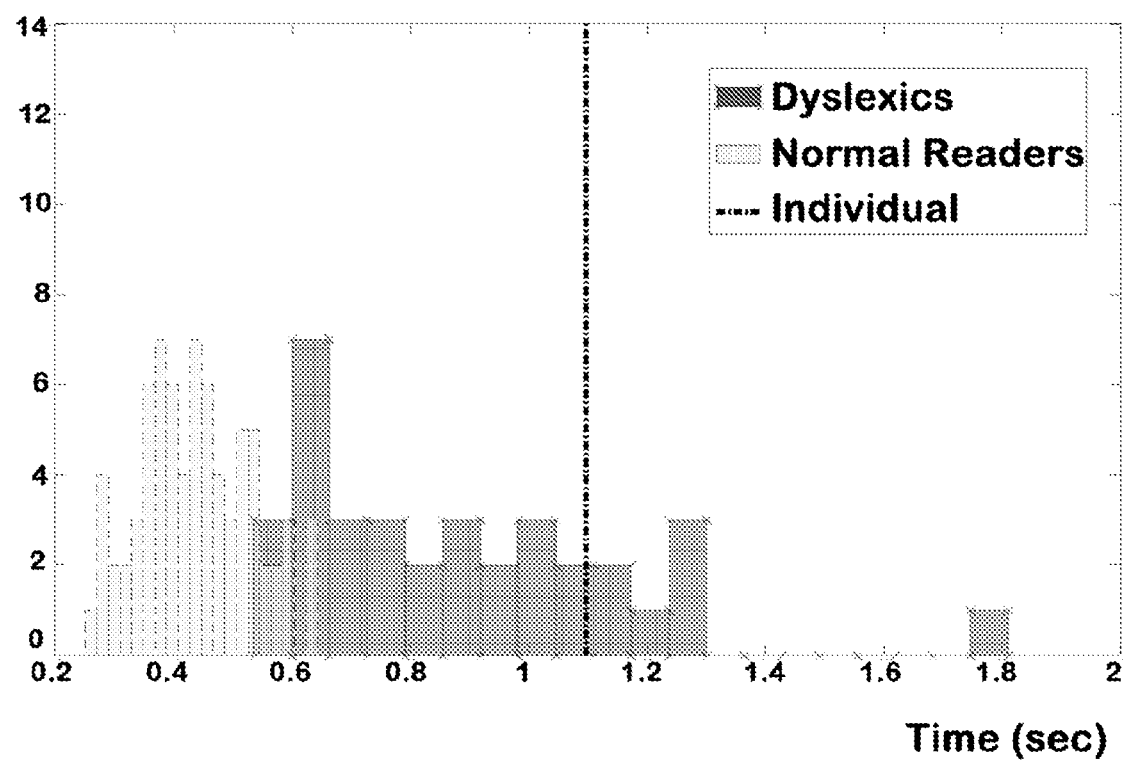

FIG. 19 is a graph showing the duration per word, exhibited in the eye movements of people with reading difficulties and normal readers as obtained from the application of the method.

Figure 20:
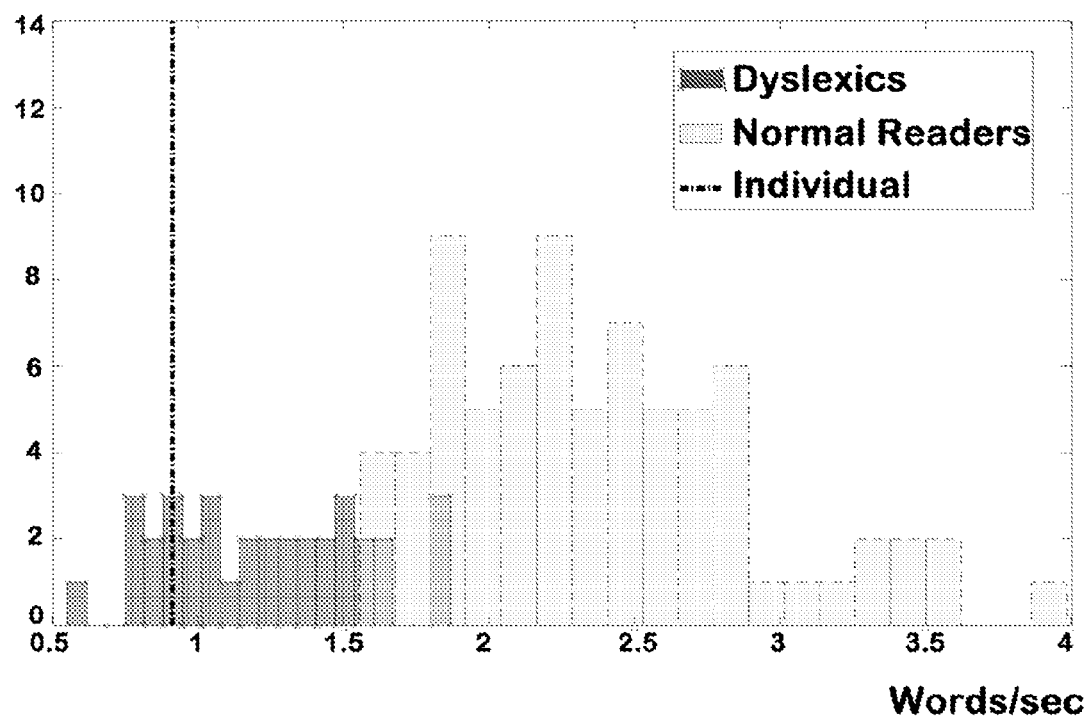

FIG. 20 is a graph showing the reading speed, exhibited in the eye movements of people with reading difficulties and normal readers as obtained from the application of the method.

Figure 21:
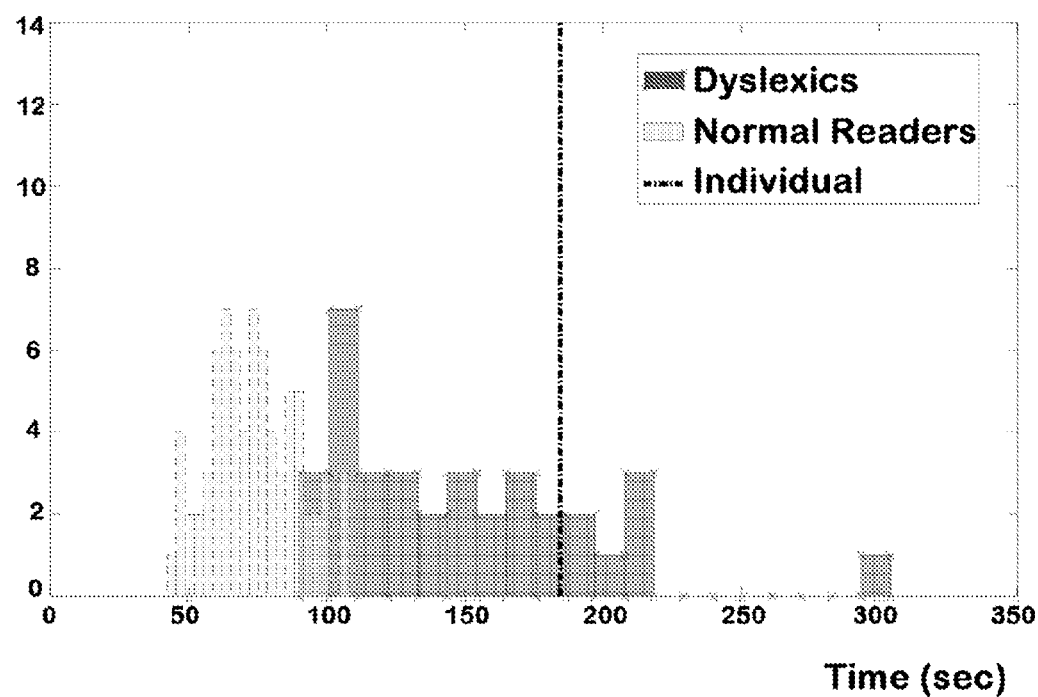

FIG. 21 is a graph showing the total reading duration, exhibited in the eye movements of people with reading difficulties and normal readers as obtained from the application of the method.

Figure 22:
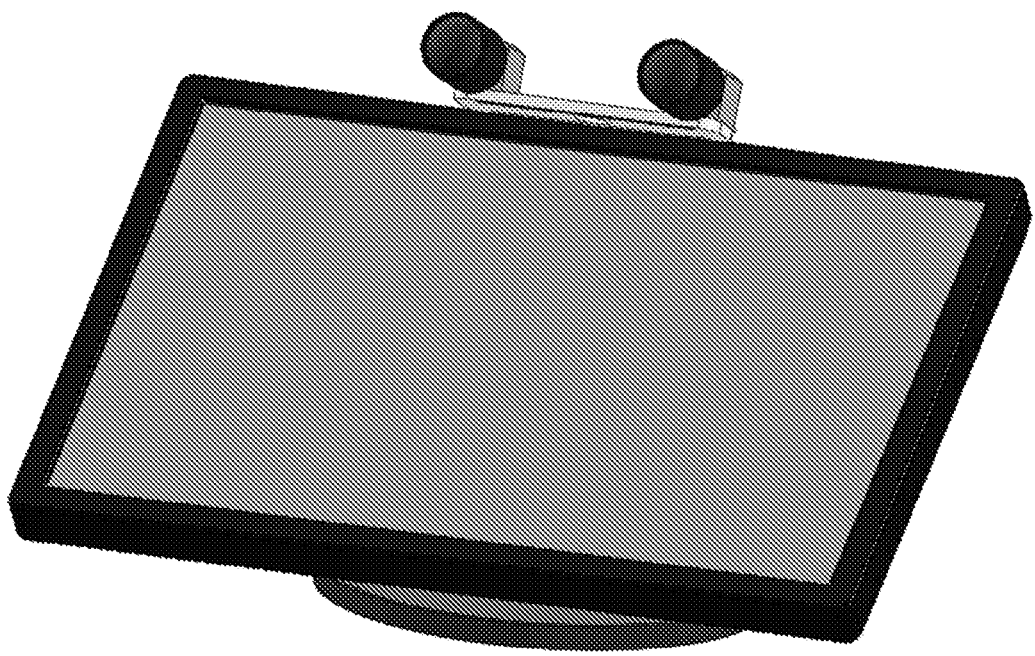

FIG. 22 depicts a hardware setup, where, the cameras are placed on top of the display device.

Figure 1:
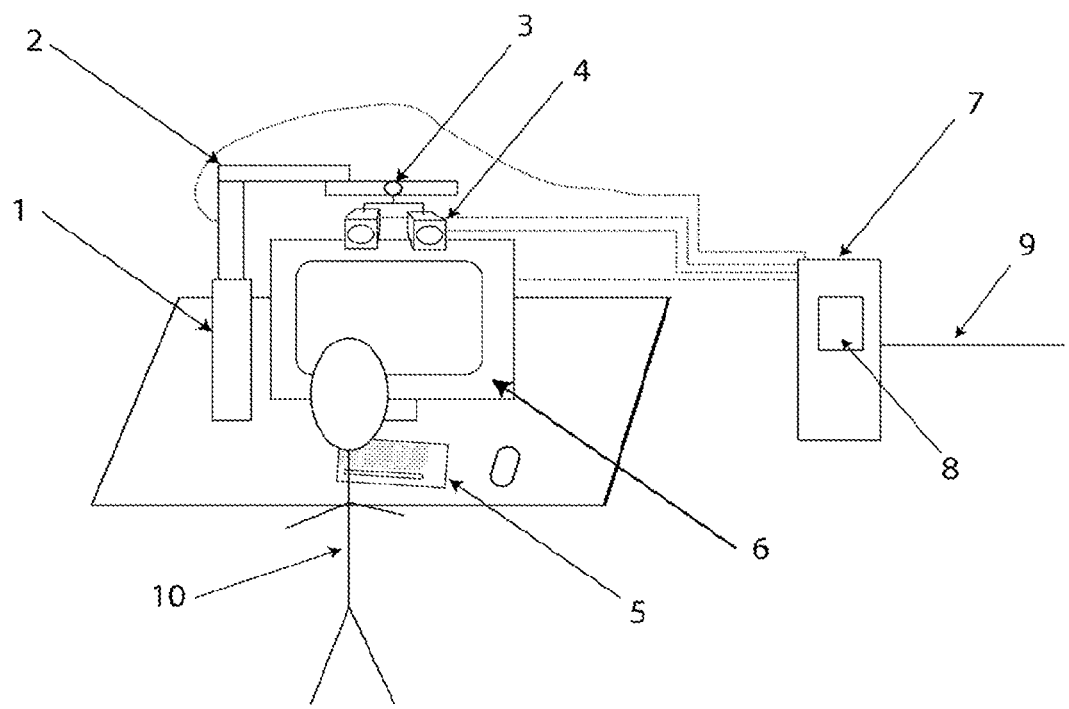
FIG. 1 shows schematically a system for performing a method of the invention.
Figure 2:
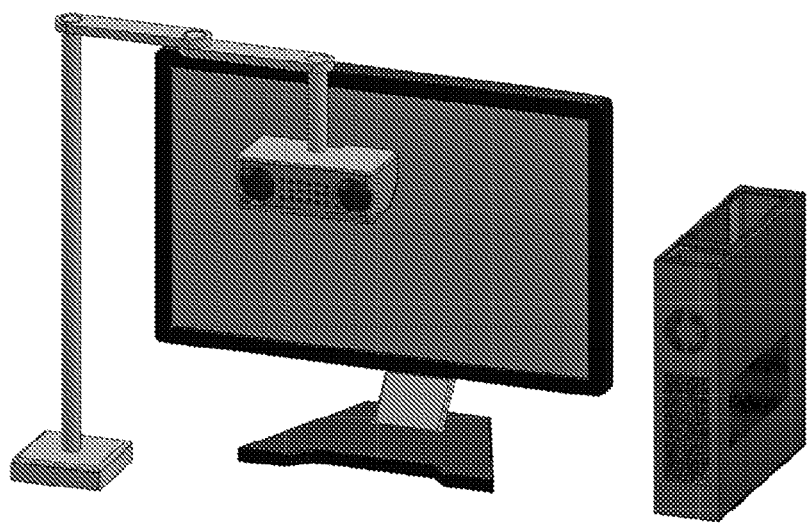
FIG. 2 show the computer hardware of the system of FIG. 1.

The system for the determination of parameters of eye fixation, which is used for the Reading Assessment for Difficulties and Abnormalities in Reading (abbrev. R.A.D.A.R.), is illustrated in FIG. 1. It is noted than the abbreviation R.A.D.A.R. in the description refers to either a system or a method according to the invention. The system of FIG. 1 includes two cameras 4 connected to a computer 7, for detecting eye movements and for tracking the position of the head. The cameras 4 are mounted on a robotic arm 1 with sensors 2 for monitoring the position of the robotic arm in relation with the subject. The system further includes infrared light sources with photodiodes and LED type lamps 3, to illuminate on the subject's eyes and be detected with computational efficiency by the cameras, a display device 6 and various input devices, such as a keyboard 5. These devices are connected with the computer 7 for recording, processing and analyzing the subject's eye movements 10.

Further, the system of FIG. 1 includes custom built software for recording, processing and analyzing the subject's eye movements and a database with recorded eye movement data defined by three coordinates, one for horizontal eye position, one for vertical eye position and one for time. Eye movement detection is achieved by illuminating the eye with infrared light and analyzing the reflection. Thus, it is possible to identify the pupil of the eye and the relative position of the bright spot, i.e. the spot that is created by the reflection of the infrared light in the eye. By combining these data, it is possible to determine the direction in which the individual gazes and focuses as well as the projection of the gaze on the display device.

A robotic arm 1 is used to support the cameras 4 used for tracking. The robotic arm 1 can move appropriately in order to optimize the position of the cameras 4 relative to the subject. Position tracking sensors 2 are connected to the computer 7 and are mounted on the robotic arm 1, so that the system can determine the appropriate position of the cameras 4 in relation to a fixed reference point, in order for the cameras to track the eye movements. The set up described above, optimizes the image quality and the video of the eye, which has to be processed. In a different setup of the invention that is illustrated in FIG. 22, the cameras are placed on top of the display device and focus along a line that intersects the display at oblique angle.

A display device 6 displays text and/or any other stimulus that an individual/subject is required to read or interact with. The display device can be a TV, a projector, a tablet, a mobile phone, an electronic opt type, electronic visual acuity charts or any other electronic display device. The display device is connected to the computer 7 and is positioned in front of the subject 10, so that he/she can clearly see what is displayed on the display device. The computer 7 can be programmed to project the desired stimulus on the display 6 so that the individual 10 can see it and, if necessary, interact with it through the control signal input devices 5, which are connected to the computer 7. The control signal input device 5 can be a keyboard, a mouse, a touch pad, a touch screen, a switch or a button. Different type of stimuli may appear on the display device such as text, drawings, images, sentences, groups of words or pseudo-words, shapes, letters, numbers, or video recordings. The reading/viewing process of the aforementioned stimuli by the subject 10 may be either silent or aloud. In another embodiment of the invention, the display device could be any type of printed material such as a book, a magazine, a newspaper, a brochure, a reading card, a visual acuity measuring card or chart or any other form of printed material. The aforementioned stimuli, either printed or electronic, may be administered under different levels of contrast or brightness/luminance.

A computer, processing means 7, is used for recording, storing and processing each gaze and fixation. Preferably the computer should have high processing power. The computer may have one or more storage devices installed-internal or external hard disk 8, floppy disk, zip drive, optical disk, or storage area on the internet/cloud. It should be able to run the custom built software and process the movements of the subject's eyes. The computer 7 could be connected with a network of computers designated by 9 in FIG. 1, such as a global computer network. This will allow the computer to exchange data with other computers connected to the network. The network could be a local area network, wide area network, an intranet or an extranet. Thus, the individual may be evaluated not only in a clinical setting, but also at a remote location, such as home, school or workplace, thereby eliminating the inconvenience of traveling long distances for testing.

Custom built software is developed for the characterization of fixations and saccades and the determination of parameters related to them. In an embodiment the software is used, among others reasons, for the calculation of duration and position for every gaze and fixation performed by the subject. The computer for recording and processing data stores a dynamic database, part of which has recordings and data from other subjects—normal readers, and readers with reading difficulties, such as dyslexia—who have been tested in the past and have a certified diagnosis for their condition, in order to compare the test's results with the results of the general population's data. This database is dynamic, meaning that it is enriched on a regular basis with new measurements from new subjects. The software may compare the results of the subject's evaluation with the results form population tests saved in the database. The subject is compared according to his/her age. For example, in case an individual has characteristics which distinguish him/her from the normal population of his/her age group, further testing is suggested, employing other assessment protocols for reading difficulties.

The R.A.D.A.R. method may be used (i) for the diagnosis of individuals who have reading difficulties, for example dyslexia, (ii) for the assessment of the efficacy of the specialist's intervention to an individual with reading difficulties, (iii) for the assessment of the development of the reading ability of normal or pathological individuals. The system and method according to the invention may be also used for the evaluation and testing ergonomic parameters of text displaying, development of reading techniques and marketing.

One use of the system embodying the R.A.D.A.R.'s eye-tracking technology is to distinguish/evaluate individuals who have reading difficulties, e.g. dyslexia, from normal subjects of the same age. The distinction/evaluation may conducted by recording of the eye movements using while the subject is reading or interacting on the R.A.D.A.R. computer and using of the custom built software for the calculation of statistical characteristics of the recorded eye movements.

The software is capable of recording, processing and analyzing parameters such as: the number of fixations, the mean value and the standard deviation of the fixation durations, the mean and the standard deviation of saccadic lengths, as well as the number of regressions and re-fixations. In addition, the software can calculate the best fitted Ex-Gaussian distribution for both fixation durations and saccadic lengths, the parameters mu ($\mu$), sigma ($\sigma$) and tau ($\tau$) of the Ex-Gaussian distribution, the mean number of fixations per a certain number of words, for example 100, or in a specific area within the display, mean reading duration per word, the reading speed and the total reading time. The software is also capable of incorporating any other parameter that may be useful in the future, for example the heart rate, hormonal status, stress, transpiration and visual acuity while correlating these parameter with the parameters described above. The software also performs multifactorial statistical comparisons.

A system and a method according to the invention may be further used to evaluate the effectiveness of a specialist's intervention on a subject with reading difficulties, e.g. dyslexia. The effectiveness of a specialist's intervention may be evaluated by following the steps below: (a) Recording of eye movements while reading and recording and analyzing all the data acquired with the use of R.A.D.A.R.'s eye-tracking technology by a computer. (b) Using software means to determine the parameters to evaluate individuals who have reading difficulties. (c) Evaluating how effective a specialist's intervention was by comparing the statistical parameters with the ones from a previous examination of the same individual.

The advantages of the R.A.D.A.R. method compared to conventional methods for evaluating reading difficulties is the system according to the invention, is able to monitor, analyze and control a number of parameters that effect the reading difficulties rather than the reading difficulties as such.

Parameters that may be evaluated by the method R.A.D.A.R. are:

Number of fixations: is the number of fixations that the individual performs while viewing the stimulus.

Mean value and standard deviation of the fixation durations, as well as the best fitted Ex-Gaussian distribution for fixation durations and the mu ($\mu$), sigma ($\sigma$) and tau ($\tau$) parameters of the best fitted Ex-Gaussian distribution.

Mean value and standard deviation of the saccadic lengths, as well as the best fitted Ex-Gaussian distribution of the saccadic lengths and the mu ($\mu$), sigma ($\sigma$) and tau ($\tau$) parameters of the best fitted Ex-Gaussian distribution.

Regressions: is the number of backward eye movements the individual does while reading and have a certain length, for example they are more than 10 characters long.

Backward re-fixations: is the number of backward eye movements the individual does while reading and have a certain length, for example they are less than 10 characters long.

Mean value of the fixations number per a certain number of words, for example 100 words: this characteristic measures the average number of fixations the individual needs to read that number of words.

Mean reading duration per word: is the average time the individual needs to read a word.

Reading speed: is the characteristic that measures how a fast the individual reads.

Total reading time: is the time the individual needs to read or process the stimulus.

With a system and method according to the invention it is possible to monitor and determined the parameters of eye fixation, with a rate of 30 Hz to 1000 Hz, i.e. one measurement per ms, preferably 60 to 120 Hz. Further "word-dependent" parameters, which may be determined and considered in the final evaluation of the reading ability of an individual are:

i. Single fixation duration, i.e. the duration of fixation in singly fixated words at first pass.
ii. Gaze duration, i.e. the duration of all fixations in multiply fixated words at first pass.
iii. Number of fixations per word, i.e. the number of fixations in multiply fixated words at first pass
iv. Number of single fixated words at first pass.
v. Number of multiple fixated words at first pass.
vi. Number of skipped words at first pass.
vii. Total reading time: is the sum of all fixation times on a particular word, including regressive fixations)

Word measures are associated with the first visit to a word and provide a way of evaluating reading difficulty caused by particular words, as opposed to difficulties associated with whole sentences. This is of particular importance if the subject has a problem in processing words.

Based on all the parameters that characterize the subject's reading ability as well as additional features that may be added by the user, the R.A.D.A.R. will determine whether the individual is conclusively or inconclusively a member of the normal population. In the latter case, it will determine how much he/she deviates from normal population, and the percentile position of this deviation for each existing or future parameter.

An example of the use of the embodiment of the invention that is illustrated in FIG. 1 is described below:

The subject 10 sits in front of the display device 6 which will display the stimulus at a constant distance. The stimulus, as explained above, can be texts, drawings, photographs, images, sentences, groups of words or pseudo-words, shapes, numbers, letters, or videos. The robotic arm 1 can be adjusted so that the cameras 4 are able to optimally record the subject's eye movements, while he/she reads or processes the stimulus projected on the display device. The setup is calibrated and the evaluation begins. The computer starts to record and store the eye movement of the individual. Once the individual completes the process of reading from or interacting with the display device, a purpose built software is used to carry out the analysis and evaluation of his/hers reading ability.

The following paragraphs present a case study with native Greek speaking population: 75 normal readers, aged 10-12 years old and 35 dyslexic readers, aged 10-12 years old, participated in this study. Eye movements were recorded while individuals were asked to read the same text. The eye-tracking system tracked and recorded the vertical and horizontal eye position. Prior to testing, all dyslexic children had an official, certified diagnosis of dyslexia, through the Hellenic Center of Mental Health and Research (H.C.M.H.R.—http://www.hcmhr.gr). A standardized reading test was also provided, to both populations and its results were consistent with their evaluations.

In the following example, an officially diagnosed—by H.C.M.H.R.—child, aged 12, was compared with both normal and dyslexic populations, and his reading ability was evaluated. In FIGS. 3 to 21 the line designated "Individual" refers to the subject/individual, the light shaded bars to the normal readers and the dark shaded bars to the dyslexics.

Figure 3:
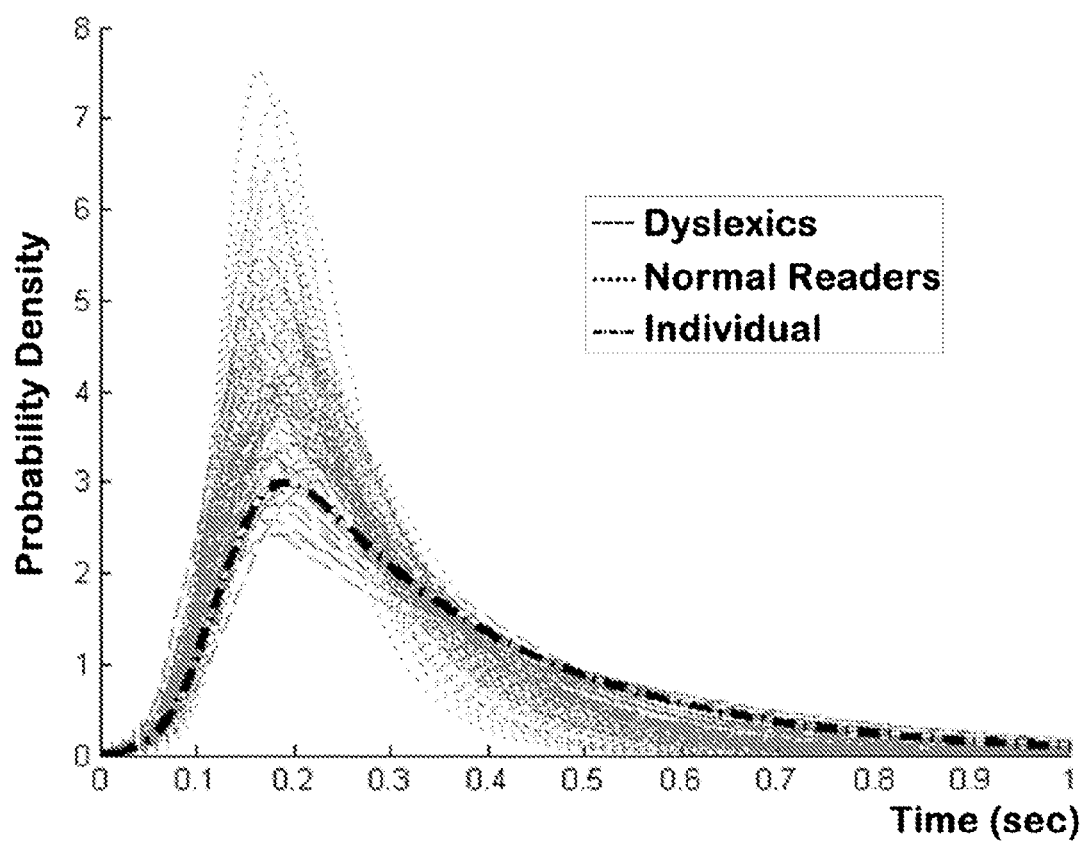
FIG. 3 is a graph showing the Ex-Gaussian curves of fixation durations, exhibited in the eye movements of people with reading difficulties and normal readers as obtained from the application of the method.
Figure 4:
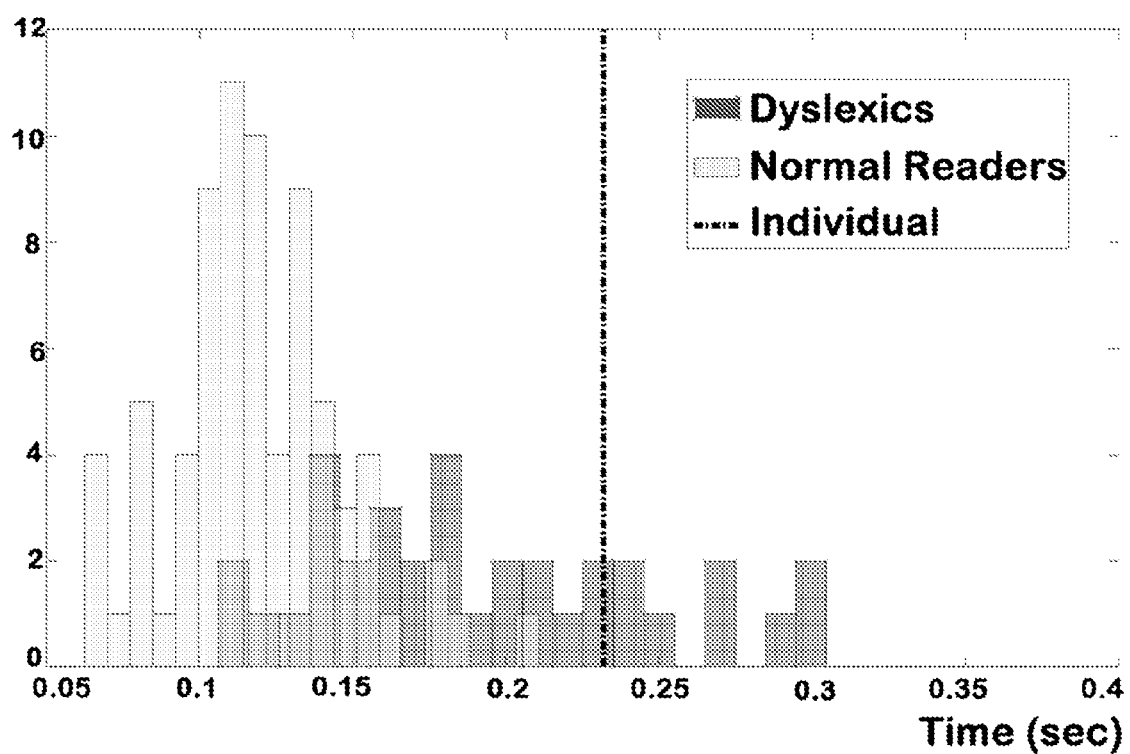
FIG. 4 is a graph showing the Ex-Gaussian parameter tau ($\tau$) of fixation durations, exhibited in the eye movements of people with reading difficulties and normal readers as obtained from the application of the method.

The first parameter used for the evaluation of reading ability is fixation durations. For each individual we calculate the frequency of the fixation durations. Afterwards, the Ex-Gaussian distribution is fitted. In FIG. 3, the Ex-Gaussian curves of the fixation durations for dyslexic population, normal readers and the individual are shown. It is clear that the individual's curve looks very similar to the dyslexic population curves. This feature does not label the individual as dyslexic, but gives the examiner a hint that the individual does not behave—according to the curve's characteristics—as a normal reader. Dyslexia diagnosis will not be called based on only one parameter but on a multitude of parameters. In FIG. 4, a parameter of paramount importance is analyzed, the tau ($\tau$) parameter of the Ex-Gaussian distribution of fixation durations. It corresponds to the exponential decay of the Ex-Gaussian distribution. This parameter is very important because it separates efficiently the normal from the dyslexic population. Based on this characteristic, the individual fits better in the dyslexic population than normal. In FIGS. 5 and 6, the parameters mu ($\mu$) and sigma ($\sigma$) from the Ex-Gaussian distribution of fixation durations are evaluated. These parameters are analyzed because they can differentiate an individual from both populations, for example if the individual suffers from an ocular problem, he/she will not belong to any of the populations. In FIGS. 7 and 8, the mean and the standard deviation of fixation durations are evaluated. Here it is also shown that the normal and dyslexic populations are separated, and that the individual best fits in the dyslexic population.

The second parameter used for the evaluation of reading ability is saccadic length. The pixels of the display device are used as the measuring unit of this parameter. Due to the fact that the distance between the individual and the display device is (almost) fixed, pixels can easily be converted to degrees. FIG. 9 shows the Ex-Gaussian curves of the saccadic lengths for dyslexic population, normal readers and the subject. It can be noted that the subject's curve is relatively similar to the dyslexic population curves. In FIG. 10, the tau ($\tau$) parameter of the Ex-Gaussian distribution of saccadic lengths is analyzed. It corresponds to the exponential decay of the Ex-Gaussian. Based on this characteristic, the individual can be placed within both the normal and the dyslexic population. Again for this feature the two populations are not clearly separated, however the feature is retained in order to include the possibility that the individual does not belong to either population. FIGS. 11 and 12 present the evaluation of the parameters mu ($\mu$) and sigma ($\sigma$) from the Ex-Gaussian distribution of saccadic lengths. The normal and dyslexic populations are clearly separated, and the subject classifies best within the dyslexic population. In FIGS. 13 and 14, the mean and standard deviation of saccadic lengths are being evaluated. Once again, the normal and dyslexic populations are clearly separated, and the subject lies to the dyslexic population.

The third parameter used for the evaluation of reading performance is the number of fixations while reading. In FIG. 15, the normal and the dyslexic populations are separated and the subject fits better to the dyslexic population. The number of fixations is correlated with diminishing reading ability.

The fourth parameter used for the evaluation of reading ability is the number of regressions and the number of backward re-fixations. Regressive eye movements are backward saccadic movements that occur when the individual re-reads part of the text. When the individual re-adjusts the fixation position on the stimulus, we have a re-fixation. In our invention, the difference between a regression and a backward re-fixation, is that regressions are defined as a backward movement longer than 10 characters and a re-fixation is a backward movement shorter than 10 characters. FIG. 16 shows the histogram of the regressions while FIG. 17 shows the histogram of the backward re-fixations. In FIG. 16 the populations are not well separated but is more likely someone who does not understand the meaning of the text to make more regressions than normal, thus the feature is retained. In FIG. 17, the re-fixation parameter separates the populations and the subject is not within the normal population.

The fifth parameter used for the evaluation of reading ability is the mean value of the number of fixations per 100 words. According to the data of FIG. 18, the subject fits better with the dyslexic readers than with the normal readers.

The sixth parameter used for the evaluation of reading ability is the mean duration per word. According to the data of FIG. 19, the individual fits better with the dyslexic readers than with the normal readers.

The seventh parameter used for the evaluation of reading ability is the reading speed of the individual. According to the data of FIG. 20, the individual fits better with the dyslexic readers than with the normal readers.

The eighth parameter used for evaluation of reading ability is the total reading time. This is a measure of the amount of time the individual needs to read the text or interact with the stimulus. According to the data of FIG. 21, the individual fits better with the dyslexic readers rather than with the normal readers.

The invention claimed is:

1. A system for subject (10) eye tracking on a projection surface (6) that includes:
   an infrared light source (3) to create reflections on the subject's eyes,
   two or more cameras (4) for subject's (10) head position tracking,
   one or more cameras (4) to track movements of the subject's (10) first eye on the projection surface (6),
   one or more cameras (4) to track movements of the subject's (10) second eye on the projection surface (6),
   a processing unit (7) configured so that it tracks the subject's (10) gazes on the projection surface (6), determines if the subject (10) focuses on a predefined sub-region or sub-regions in the projection surface (6) from the tracking of said gazes and computes the duration of said gazes, and
   wherein the camera (4) used to detect and determine the gaze coordinates of the first eye and the camera (4) used to detect and determine the gaze coordinates of the second eye are on a movable arm with sensors (2) to monitor the position of the cameras (4) relative to the projection surface (6).

2. The system according claim 1, whereby the projection surface (6) presents a text including a plurality of words and the processing unit (7) is configured so that it determines from the gaze tracking, if the subject (10) focuses on certain words in the projection surface (6), and it computes the duration of these gazes on said words.

3. The system according to claim 1, whereby the one camera (4) for tracking the subject's (10) first eye's movements on the projection surface (6) and the other camera (4) for tracking the second eye's movements on the projection surface (6) are the two cameras (4) used for the subject's (10) head tracking and the processing unit (7) is configured so that it determines motions of the subject's (10) head.

4. The system according to claim 1, whereby the camera (4) used to detect and determine the gaze coordinates of the first eye and the camera (4) used to detect and determine the gaze coordinates of the second eye are movable and are at a known position relative to the projection surface (6).

5. The system according to claim 1, whereby the processing unit (7) is configured so that it tracks the subject's (10) gazes from both eyes on the projection surface (6), determines if the subject (10) focuses on a predefined sub-region or sub-regions in the projection surface (6) from the tracking of said gazes of at least one eye and computes the duration of said gazes.

6. The system according to claim 1, whereby the one or more cameras (4) to track movements of the subject's (10) first eye on the projection surface (6) and the one or more cameras (4) to track movements of the subject's (10) second eye on the projection surface (6) are configured to track said gazes with a sampling rate between 30 Hz and 1000 Hz and whereby the processing unit (7) is configured so that it computes the duration of said gazes with a rate that is approximately equal with the sampling rate.

7. A method for subject's (10) eye tracking on a projection surface (6) using the system according to claim 1, whereby the methodology includes the following steps:
   using of a projection surface that includes text with words and/or shapes and/or numbers and/or images and/or video with the projection surface being printed or electronically displayed,
   determining parameters of fixations on predefined sub-regions or sub-regions inside the projection surface (6), and
   determining parameters of gaze movements inside the projection surface (6) from the fixations parameters.

8. The method according to claim 7 that includes gaze tracking of at least one eye, determining saccadic motion parameters from the gaze tracking of at the least one eye and computing the number and duration of fixations from the saccadic motion parameters.

9. The method according to claim 8, whereby the parameters of saccadic motion include the length of the saccadic motion.

10. The method according to claim 7, whereby the fixation parameters include the number and duration of fixations.

11. The method according to claim 7, where the parameters of gaze movements include at least one of the number, duration, direction and the length of eye movements.

12. The method according to claim 7, whereby the fixation parameters include the number of fixations on the same sub-region of the projection surface (6).

13. The method according to claim 7, whereby the method includes the determination of mean values and/or standard deviation of the fixation parameters and/or gaze movements in the projection surface (6).

14. The method according to claim 10, whereby the method includes the determination of parameters of Gaussian exponential distributions for the duration of fixations inside the projection surface (6).

15. The method according to claim 7, whereby the method includes the determination of average values and/or standard deviation and/or parameters of Gaussian exponential distributions for saccadic motion parameters.

16. The method according to claim 7, whereby the projection surface includes text with words and the method includes the determination of at least one of the following parameters:
   the duration of fixation in singly fixated words at first pass,
   the duration of all fixations in multiply fixated words at first pass,
   the number of fixations in multiply fixated words at first pass,
   the number of single fixated words at first pass,
   the number of multiple fixated words at first pass,
   the number of skipped words at first pass of said sub-region, and
   the sum of all fixation times on a particular word, including regressive fixations.

* * * * *